United States Patent
Alnafisah (10) Patent No.: US 8,976,022 B2
(45) Date of Patent: Mar. 10, 2015

(54) MOBILE TRACKING IDENTIFICATION SYSTEM, METHOD, AND COMPUTER PROGRAM PRODUCT

(76) Inventor: Khalid Hamad Motleb Alnafisah, Ruston, LA (US)

( * ) Notice: Subject to any disclaimer, the term of this patent is extended or adjusted under 35 U.S.C. 154(b) by 400 days.

(21) Appl. No.: 13/446,037

(22) Filed: Apr. 13, 2012

(65) Prior Publication Data

US 2013/0271280 A1    Oct. 17, 2013

(51) Int. Cl.
*G08B 1/08*    (2006.01)
(52) U.S. Cl.
USPC ............. 340/539.13; 340/539.15; 340/539.21
(58) Field of Classification Search
CPC ...... G06K 7/0008; G06K 17/00; G06Q 50/22
USPC ............................. 340/539.13, 539.15, 539.21
See application file for complete search history.

(56) References Cited

U.S. PATENT DOCUMENTS

| | | | | |
|---|---|---|---|---|
| 5,914,671 A * | 6/1999 | Tuttle | ......................... | 340/10.42 |
| 7,411,506 B2 * | 8/2008 | Volpi et al. | ................. | 340/572.4 |
| 7,676,380 B2 * | 3/2010 | Graves et al. | ..................... | 705/2 |
| 7,707,044 B2 * | 4/2010 | Graves et al. | ..................... | 705/2 |
| 7,750,810 B2 | 7/2010 | Ritter et al. | | |
| 7,817,014 B2 * | 10/2010 | Krishna et al. | ............... | 340/10.4 |
| 7,843,350 B2 * | 11/2010 | Geissler et al. | ............ | 340/573.2 |
| 7,917,439 B2 * | 3/2011 | Barnes, Jr. | ...................... | 705/51 |
| 7,932,825 B2 | 4/2011 | Berger | | |
| 7,961,093 B2 * | 6/2011 | Chiao et al. | ............. | 340/539.26 |
| 8,299,914 B2 * | 10/2012 | Culpepper et al. | ....... | 340/539.13 |
| 8,493,205 B2 * | 7/2013 | Bhattacharya et al. | .. | 340/539.13 |
| 2003/0050595 A1 | 3/2003 | Campbell | | |
| 2004/0078219 A1 * | 4/2004 | Kaylor et al. | ..................... | 705/2 |
| 2004/0208343 A1 | 10/2004 | Golden et al. | | |
| 2004/0257224 A1 * | 12/2004 | Sajkowsky | ............... | 340/539.13 |
| 2005/0101841 A9 * | 5/2005 | Kaylor et al. | ................. | 600/300 |
| 2005/0134452 A1 | 6/2005 | Smith | | |
| 2006/0059421 A1 * | 3/2006 | Benbrahim et al. | .......... | 715/513 |
| 2006/0212096 A1 | 9/2006 | Stevenson | | |
| 2006/0220955 A1 * | 10/2006 | Hamilton | ................. | 342/357.13 |
| 2006/0236373 A1 * | 10/2006 | Graves et al. | ..................... | 726/3 |
| 2006/0276204 A1 * | 12/2006 | Simpson et al. | ........... | 455/456.5 |
| 2007/0001813 A1 * | 1/2007 | Maguire et al. | .............. | 340/10.2 |
| 2007/0032266 A1 * | 2/2007 | Feher | ......................... | 455/553.1 |
| 2007/0032832 A1 * | 2/2007 | Feher | .............................. | 607/32 |
| 2007/0103303 A1 * | 5/2007 | Shoarinejad | ............... | 340/572.1 |
| 2007/0118253 A1 * | 5/2007 | Dahler | .............................. | 701/1 |
| 2007/0120683 A1 | 5/2007 | Flippen et al. | | |
| 2007/0210923 A1 * | 9/2007 | Butler et al. | ............... | 340/572.8 |
| 2008/0040157 A1 * | 2/2008 | Saunders | .......................... | 705/3 |
| 2008/0094228 A1 * | 4/2008 | Welch et al. | ............... | 340/573.1 |

(Continued)

*Primary Examiner* — Jennifer Mehmood
*Assistant Examiner* — Rufus Point
(74) *Attorney, Agent, or Firm* — Oblon, McClelland, Maier & Neustadt, L.L.P.

(57) ABSTRACT

A mobile tracking identification system, method, and computer program product uses a tracking chip, a pickup apparatus, a wireless network, and a controller unit. The tracking chip is disposed within a human body and is configured to passively transmit a data beacon via a wireless link. The pickup apparatus is configured to generate a triggering signal that activates the tracking chip as well as receive a data beacon from the tracking chip. The wireless network is configured to relay the data beacon from the pickup apparatus via a transmission medium. The controller unit is configured to receive the data beacon from the wireless network and generate geolocational data, store the geolocational data to produce a tracking vector, and initiate a commandeering function as needed.

15 Claims, 7 Drawing Sheets

(56) References Cited

U.S. PATENT DOCUMENTS

| | | | |
|---|---|---|---|
| 2008/0100447 A1* | 5/2008 | Powell | 340/572.2 |
| 2008/0117022 A1* | 5/2008 | Polozola | 340/10.1 |
| 2008/0157928 A1* | 7/2008 | Butler et al. | 340/10.1 |
| 2008/0180242 A1 | 7/2008 | Cottingham | |
| 2008/0208753 A1* | 8/2008 | Lee et al. | 705/51 |
| 2010/0156601 A1* | 6/2010 | Lin et al. | 340/10.1 |
| 2011/0148884 A1* | 6/2011 | Zeleny | 345/441 |
| 2012/0012069 A1* | 1/2012 | Hempstead et al. | 119/712 |
| 2012/0119883 A1* | 5/2012 | Bekritsky | 340/10.4 |

\* cited by examiner

MOBILE TRACKING IDENTIFICATION SYSTEM, METHOD, AND COMPUTER PROGRAM PRODUCT

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

BACKGROUND

1. Field of the Disclosure

Embodiments described herein relate generally to a system, method, and computer program product for tracking and storing information of a human. More particularly, the embodiments described herein relate generally to a system that can locate, track, and provide personal information about a human who has an implanted identification chip.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

SUMMARY

According to an embodiment, there is provided a mobile tracking and identification system. The system includes a tracking chip, a pickup apparatus, a wireless network, and a controller unit. The tracking chip is disposed within a human body and configured to passively transmit a data beacon via a wireless means. The pickup apparatus is configured to generate a triggering signal that activates the tracking chip as well as receive a data beacon from the tracking chip. The wireless network is configured to relay the data beacon from the pickup apparatus via an appropriate transmission medium. The controller unit is configured to receive the data beacon from the wireless network and generate geolocational data, store the geolocational data to produce a tracking vector, and initiate a commandeering function as needed. The commandeering function initiates the triggering signal of one or more pickup apparatus's located in a specified geographical region as specified by the user.

According to another embodiment, there is also provided a method of a tracking system for a tracking chip disposed within a human body. The method includes transmitting a data beacon via a wireless means from an activated tracking chip disposed within a human body, picking up the data beacon from a remote or mobile receiving unit, relaying the data beacon to a controller unit, receiving the data beacon from the remote or mobile receiving unit, the data beacon being transmitted over a transmission medium, generating geolocational data of the tracking chip based on location data contained within the coded signal, initiating a commandeering function through one or more wireless networks to actively prosecute the location of the tracking chip, and presenting location data of the tracking chip to a user.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Radio Frequency Identification (RFID) is a technology for the unambiguous and contactless identification of objects, goods, animals, or persons. It enables a quick and automatic data capture by means of radio waves, so that the information can be selected and transmitted considerably more quickly and conveniently. An RFID system requires essentially of one or more RFID chips or tags and a suitable RFID reading device. RFID tags are ordinarily flat chips in an array of various sizes, which are able to send data by radio waves to a reading device via an antenna. They can have one or more storage devices which are able to store different quantities of data, depending upon the design.

There are basically two types of RFID tags: active tags and passive tags. Active RFID tags are provided with their own power supply, and can transmit a wireless RFID signal until their power sources have been exhausted. Duration of active RFID tags are dependent upon their power source as well as their transmitting characteristics. Passive RFID tags have no dedicated power source and only receive power when an RFID signal is applied to the tag via the passive RFID tag antenna. With this antenna, the tag, when activated through the reading device, can generate the required energy for the data transmission practically by itself. These passive chips have an almost endless service life.

There are numerous applications for RFID technology such as supply logistics, identification, and tracking. Since the development of implantable chips, RFID technology is also playing more and more of an important role in the area of human identification. There exist today transponders the size of a grain of rice, packed in glass, which using local anesthesia can be injected in a pain-free method under the human skin and which cannot be discerned by the human eye. These radio capable transponders contain a unique individual identification number which only occurs once. An independent tag is thus created. When this identification tag is within the vicinity of an RFID scanner, it emits this personal identification number. The wanted signal is modulated via the feed signal whereby bidirectional communication is also made possible.

RFID technology also plays an especially important role in the area of implantable identification tags for the health, education, finance, and security fields. Data can be written to an implanted RFID tag and subsequently read by an RFID reader. The benefit of this is that as the RFID tag is implanted within the skin or muscle, it is always available for quick and easy access, especially in an emergency situation.

While most RFID applications are implemented through the use of microchips, the present inventor recognizes that recent advances in nanotechnology show promise of applying certain features of both tracking and information storage at the nano level. Features of RFID chips that could contain nanotechnology implementations include memory storage, power generation, or even transmitting and receiving radio wave signals.

Referring now to the drawings, wherein like reference numerals designate identical or corresponding parts throughout the several views.

Figure 1:
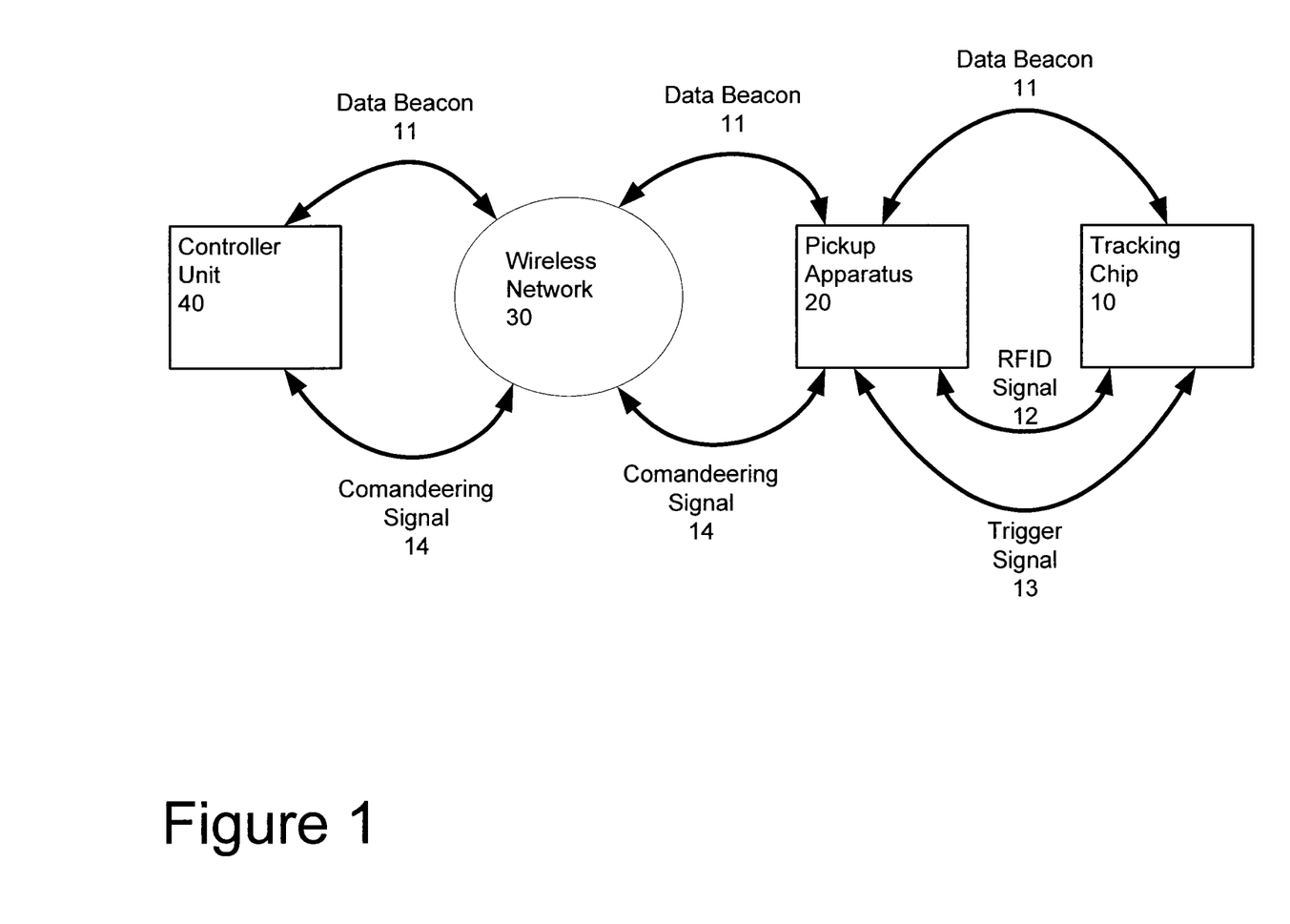
FIG. 1 is a data flow chart showing an information flow amongst the components of an exemplary tracking system.

FIG. 1 is a system level overview of an exemplary mobile tracking and identification system. A tracking chip 10 which has been disposed in a human body transmits a data beacon to a pickup apparatus 20 either passively when a triggering signal is applied to a passive RFID antenna or actively via an autonomous beacon signal via an active RFID chip. When the data beacon is received by the pickup apparatus 20, the pickup apparatus 20 transmits the data beacon to a controller unit 40 via a wireless network 30.

In an exemplary embodiment, the pickup apparatus 20 is a cellular phone with a mobile RFID reader. The mobile RFID reader may be configured to read RFID tags in a similar manner as laid out in U.S. Patent Publication No. 2010/0289617 which is herein incorporated by reference. When commanded by the controller unit 40, the cellular phone transmits a triggering signal via the mobile RFID reader. If there is a supported passive RFID tracking chip disposed within a human body within range of the RFID reader, the RFID tracking chip will become activated and will broadcast a data beacon. The RFID reader will determine if the signal format of the data beacon is of a supported format. If the signal format is supported by the mobile RFID reader, the cellular phone will transmit both location data and the data beacon to the controller unit 40 via the wireless network 30 in which the cell phone is registered. By commanding the cell phone to activate its RFID reader functionality in order to activate the RFID tracking chip and receive the generated data beacon, mobile identification and tracking can be achieved.

In another embodiment, the passive RFID tracking chip can be configured to be activated by radio frequencies used by public wireless networks found in high traffic areas such as shopping malls or airports. When the passive RFID tracking chip is within service of a wireless network, the passive RFID chip becomes activated and broadcasts a data beacon. A router providing the wireless network will determine if the signal format of the data beacon is supported. If so, the router providing the wireless network will transmit the both location data and the data beacon to the controller unit 40 via the internet.

In another embodiment, the passive RFID tracking chip can be configured to be activated by a high frequency satellite broadcast. When commanded by a controller unit 40, a satellite transmits a triggering signal through its broadcast beam. If there is a supported passive RFID tracking chip disposed within a human body within line of sight of the satellite's broadcast beam, the RFID tracking chip will become activated and broadcast the data beacon. That data beacon may be relayed through local transmitter devices (e.g., cell phone or cell tower) to the satellite. The satellite will determine if the data beacon is supported. If so, the satellite will transmit both location data and the data beacon to the controller unit 40 via the satellite's associated satellite network.

While examples of an exemplary pickup apparatus 20 may include a cell phone, a wireless network router, or a satellite, the present disclosure is not limited by these examples. A tracking chip 10 can be configured to broadcast a plurality of data beacons that can be supported by a plurality wireless transmission frequencies and a plurality of wireless protocols. Thus, an appropriate pickup apparatus 20 may be any device that operates within the broadcast capability of the tracking chip 10.

Figure 2:
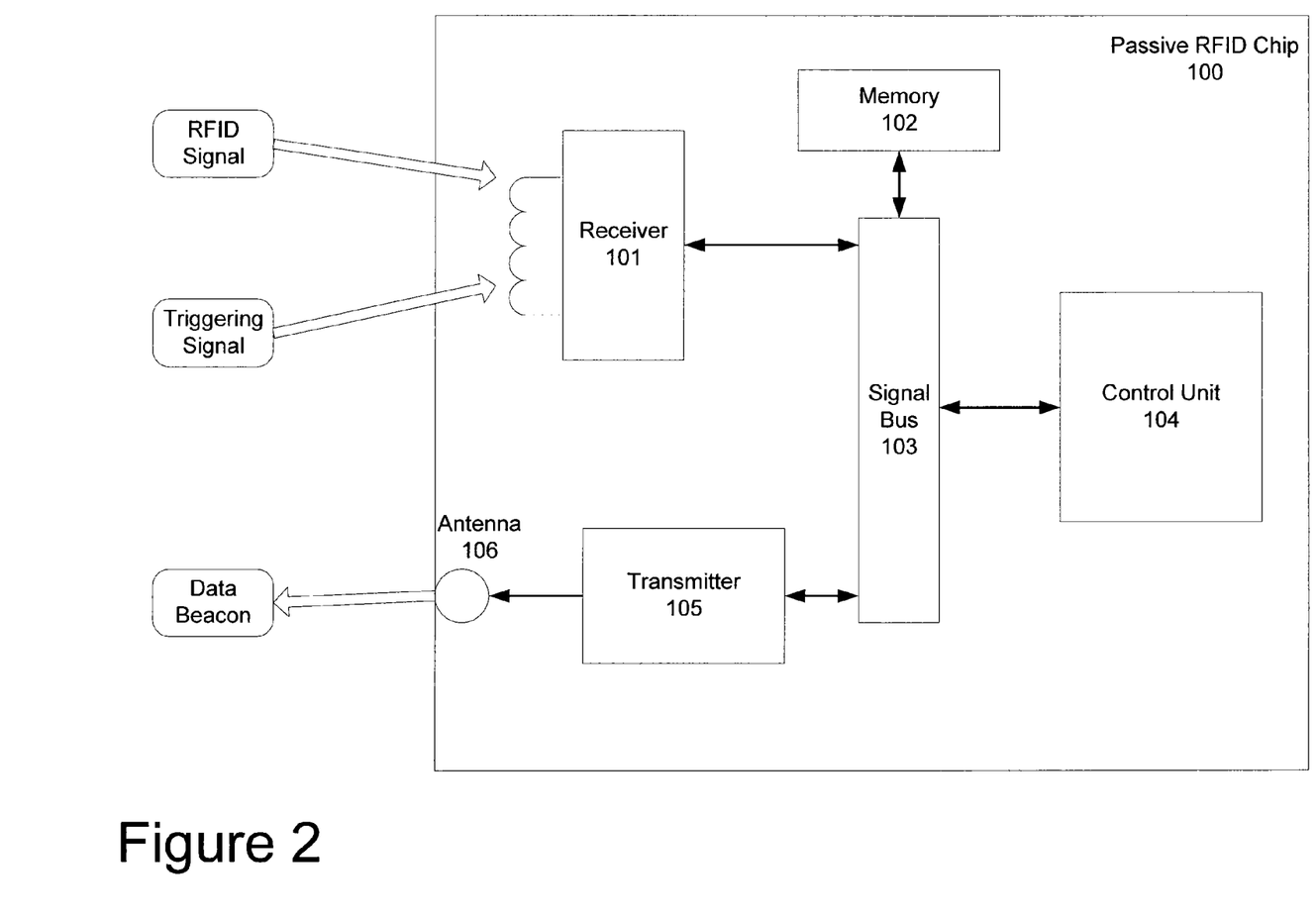
FIG. 2 is a block diagram of an exemplary passive tracking chip to be disposed within a human body.

An exemplary passive RFID chip 100 disposed in a human body is shown in FIG. 2. When either an RFID signal or a triggering signal is applied to the passive RFID chip 100, the receiver 101 receives the signal while simultaneously using the applied signal to power the rest of the components of the passive RFID chip 100. Once the passive RFID chip 100 becomes activated, the receiver 101 determines the source of the RFID signal or triggering signal. Once the source of the signal, such as a cell phone, wireless network router, satellite, or the such, has been identified, the receiver 101 sends an identification signal to the control unit 104 via the signal bus 103. The control unit 104 then reads a data beacon message stored in memory 102 via a signal bus 103 which corresponds to the wireless platform of the device in which the RFID signal or triggering signal was transmitted. The control unit 104 then sends the data beacon to the transmitter 105 which encodes and modulates the data beacon. The transmitter 105 then broadcasts the data beacon via the antenna 106. The broadcast data beacon may be received by the pickup apparatus 20 that originally transmitted the RFID signal or triggering signal if the pickup apparatus 20 is still within range. Any other pickup apparatus 20 that is also within range and is appropriately configured will receive the data beacon as well and subsequently relay it. For example, if a first cell phone transmits a triggering signal and the passive RFID tracking chip 100 responds with a data beacon, not only will the first cell phone receive the data beacon, but any other cell phone within range of passive RFID tracking chip 100 broadcast will receive the data beacon as well.

In another embodiment, the receiver 101 may be configured to recognize and react to a plurality of incoming wireless signal frequencies. These frequencies may be derived from various wireless mediums or protocols such as, but not limited to, cellular, Bluetooth, NFC, wireless local area network (WLAN), or satellite signals. The receiver 101 will determine if either the RFID signal or triggering signal received by the passive RFID chip is from a supported source. A source is determined to be supported if has the ability to receive and relay a data beacon back to the controller unit 40. If the source is determined to be a supported source, an appropriate data beacon will retrieved from the memory 102 and broadcasted via the antenna 106.

For example, if a first cell phone using carrier A that employs a GSM network comes within range of an exemplary passive RFID chip 100 and transmits an RFID signal or a triggering signal, the passive RFID chip 100 may receive the signal and determine that network that the cell phone is operating on is not connected to or supported by the controller unit 40. In this case, no transmission message will be broadcasted. If a second cell phone with carrier B that employs a CDMA network comes into range of the passive RFID chip 100 and transmits an RFID signal or a triggering signal, the passive RFID chip 100 may receive the signal and determine that the network that the second cell phone is operating on is in supported by the controller unit 40. The passive RFID chip will then broadcast a data beacon as to be received by the second cell phone and any other cell phone using the same network that is within range.

In another embodiment, the RFID chip disposed within a human body can also be an active RFID chip. The active RFID chip could have a similar configuration as that of the passive RFID chip 100 but would include a battery unit that provides continuous or intermittent power to all or a selection of the components of the active RFID chip. The active RFID chip can be configured to periodically broadcast a data beacon even if an RFID signal or a triggering signal is not present or when there is not a supported pickup apparatus 20 in the area. The continuously broadcasted data beacon can correspond to a single data format as to be recognized by a single type of pickup apparatus 20 or cycle through a plurality of data formats as to be recognized by a plurality of pickup apparatus' 20. The active RFID chip can also be configured to operate in a similar manner as the passive RFID chip 100 as to receive either a RFID signal or a triggering signal. The received signal can be used to restore charge to the battery unit of the active RFID chip. The received signal can also be used to only transmit the appropriate beacon signal that corresponds to the received signal which would be preferable if the active RFID chip is configured to cycle through multiple beacon signal formats.

In another embodiment, the RFID chip disposed within a human body can be developed and fabricated using nanotechnology implementations in order to be more seamlessly and discretely integrated within the human body. Certain features and components of the RFID chip may be constructed or implemented using nanotechnology implementations such as memory storage, power generation, or even transmitting and receiving radio wave signals as laid out in U.S. Patent Publication No. 2010/0001846 which is herein incorporated by reference.

When a data beacon has been broadcasted and subsequently received by a supported pickup apparatus 20, the pickup apparatus 20 will append additional data to the data beacon that corresponds to the present location of the pickup apparatus 20. Location information can take on any number of forms to include information such as GPS coordinates, cellular tower code, IP address, or satellite code. After the pickup apparatus 20 adds the additional data to the data beacon, the pickup apparatus will then relay the data beacon to the controller unit 40 via the appropriate wireless network 30 in which the pickup apparatus 20 is operating. Wireless networks in which the data beacon is relayed can be any number of wireless transmission mediums or protocols including as a cellular network protocol such as CDMA or GSM, a wireless local area network using an 802.11 protocol that is connected to the internet, or a more specialized network such as a satellite network.

Figure 3:
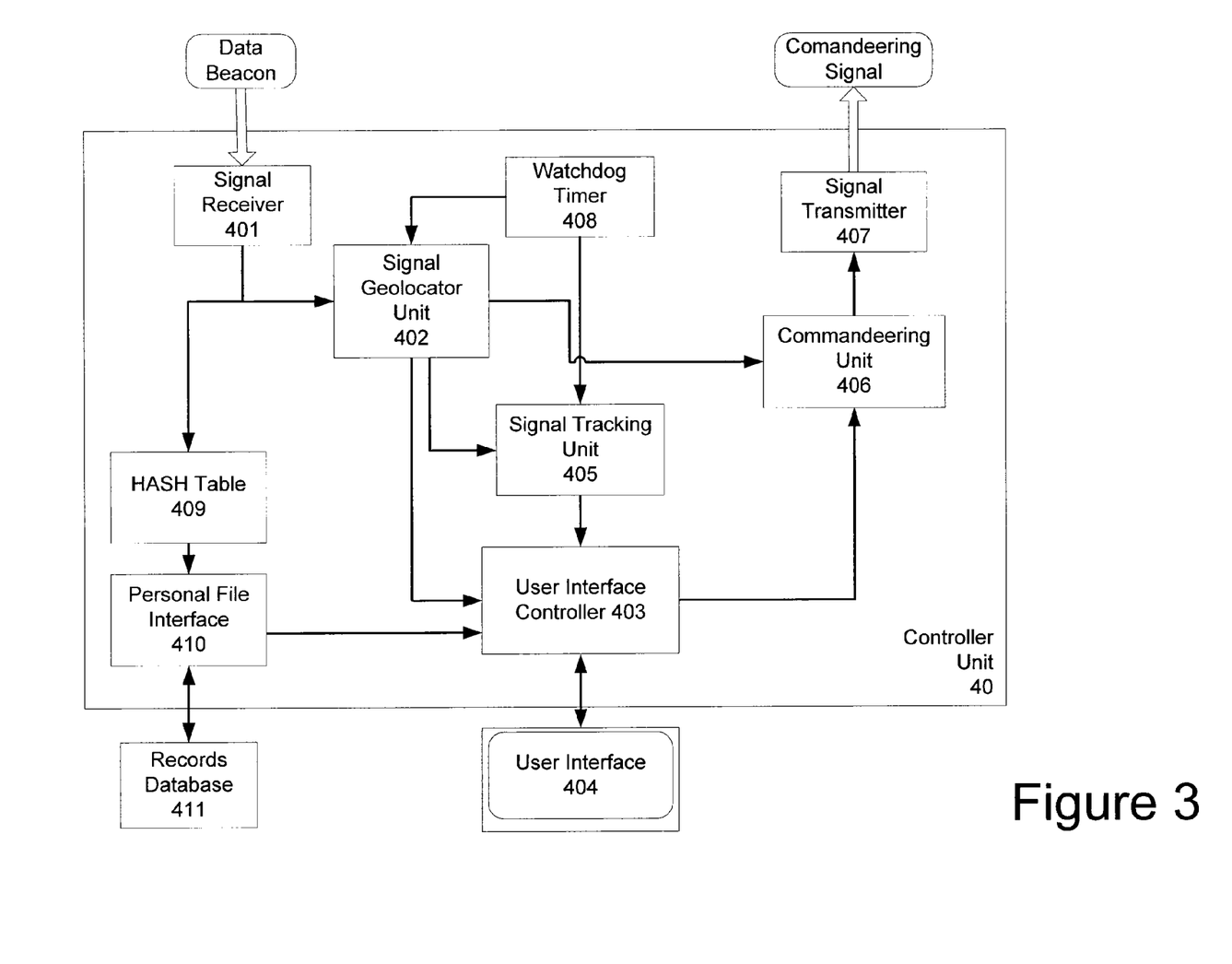
FIG. 3 is a functional block diagram of an exemplary controller unit.

When the data beacon has been relayed to the controller unit 40, the controller unit 40 receives the data beacon at the signal receiver 401 which decodes and demodulates the signal and prepares the signal for further processing as shown in FIG. 3. The data beacon is then sent to a signal geolocator unit 402 that generates geolocation data of the pickup apparatus 20 based on the location data the pickup apparatus 20 had previously appended. Location data can take a plurality of formats to include GPS coordinates if the pickup apparatus 20 is a GPS enabled device, location data from one or more cell towers in which the pickup apparatus 20 is operating on, or IP data from a WLAN router connected to the interne. Depending on the detection information provided by the data beacon, the signal geolocator unit 402 can provide geolocational data with a range of accuracies from precise latitude and longitude coordinates to general vicinity data. This information is sent to the user interface controller 403 which generates user data for display on the user interface 404.

The signal geolocator unit 402 also sends the geolocation data to the signal tracking unit 405. The signal tracking unit 405 stores one or more pieces of geolocation data that correspond to specific tracking chips 10 that was activated by one or more pickup apparatus's 20. Over time, a plurality of geolocational data for a specific tracking chip 10 may be received by the signal tracking unit 405. As geolocational data is added to the signal tracking unit 405, trend analysis can be performed on a plurality of geolocational data for one or more of a specific tracking chip 10. Geolocational data from a single pickup apparatus 20 or a plurality of pickup apparatuses' 20 are combined and a tracking vector with both directional and speed parameters can be generated. Weights can be assigned to geolocational data that is used to generate a tracking vector with more accurate geolocational data, such as GPS coordinates, receiving a higher weights and more general geolocational data, such as cell tower location, receiving lower weights.

One such possible algorithm could included a simple weighted average of a plurality of pickup apparatuses and would take the form of:

$$\text{TrackingVector} = \Sigma(w_{GPS} \times \text{Data}_{GPS} + w_{WLAN} \times \text{Data}_{WLAN} + w_{CELL} \times \text{Data}_{CELL})$$

where w is the weight applied to the source data component of the tracking vector. While a weighted average algorithm is presented as a simple example to generate a tracking vector, any method or algorithm can be used to develop a tracking vector. Tracking vectors generated by the signal tracking unit 405 are sent to the user interface controller 403 which generates user data for display on the user interface 404.

Based on the geolocation data and tracking vectors obtained from a data beacon corresponding to a specific tracking chip 10, a user may want to obtain additional tracking information of a specific tracking chip 10 or attempt to gain initial geolocation information of a specific tracking chip 10. In this case, the user would initiate from the user interface 404 a commandeering function contained within the commandeering unit 406.

When initiated, the commandeering unit 406 generates a commandeering signal based on the wireless network defined by the user. Different wireless networks may be selected by the user based on the probability of a data beacon return or operational availability of the wireless network. The commandeering signal would be generated in a appropriate manner so as to be relayed to one or more pickup apparatus's 20 over the appropriate wireless network 30 using the necessary frequencies and protocols of the wireless network 30. The commandeering signal will be transmitted via the signal transmitter 407 to all of the pickup apparatus's 20 within range of the wireless network transmitting the commandeering signal. If a pickup apparatus 20 receives a commandeering signal, it will then broadcast a triggering signal to the surrounding vicinity of the pickup apparatus 20. If a tracking chip 10 is within range of the pickup apparatus 20 that broadcasted the triggering signal, the tracking chip 10 will activate and subsequently broadcast a data beacon in a similar fashion as previously discussed.

In another embodiment, the controller unit 40 also contains a watchdog timer 407. The watchdog timer 407 provides a timing input to both the signal geolocator unit 402 and the signal tracking unit 405. The signal geolocator unit 402 initiates a setting time when an initial data beacon corresponding to a specific tracking chip 10 arrives with geolocational data provided by a pickup apparatus 20. Whenever a new piece of geolocational data for a specific tracking chip 10 arrives at the signal geolocator unit 402, the signal geolocator unit 402 resets the setting time. If the setting time exceeds a predetermined period (i.e., now new geolocational data received to reset the timer), the signal geolocator unit 402 may automatically initiate the commandeering unit 406 in order to attempt to retrieve additional geolocation data from a specific tracking chip 10. This automatic feature can be toggled on and off by the user.

The watchdog timer 407 also provides a timing input to the signal tracking unit 405. The signal tracking unit 405 has the option to timestamp each piece of geolocation data as it is received by the signal tracking unit 402. The timestamp of the geolocation data provides an input into determining the potential weight assigned to that piece of geolocations data. Weights can be assigned within the tracking vector algorithm based on the age of a piece of geolocation data. The algorithm could apply a lower weight to older geolocation data and apply a higher weight to newer geolocation data.

In another embodiment, the controller unit 40 could also contain a hash table 409 that uses a hash key embedded within the data beacon to generate a unique identification value corresponding to a specific tracking chip 10. Once a unique identification value has been generated by the hash table 409, the personal file interface 410 uses the unique identification value to retrieve an information record from a records database 411 that corresponds to the identification of the tracking chip 10. The information record obtained from the records database 411 can contain a plurality of unique identification profiles that contain personal, criminal, health, or educational information of individuals based on the hash key provided by the tracking chip 10. The unique identification profiles is sent to the user interface controller 403 which generates user data for display on the user interface 404. Data within the record can be read or modified from the user interface 404 as needed before being stored back in the records database 411.

In another embodiment, the records database 411 holds personal health information of an individual which can be accessed by a health care provider by initiating a commandeering signal to read the tracking chip 10 disposed within a patients body. The data beacon returned from the tracking chip 10 via a pickup apparatus 20 provides a social security number which can be used as a hash key for the hash table 409 to access the patients health record from the records database 411. The doctor can review medical history, allergies, DNA information and other related medical information from the user interface 404 as well as make modifications and updates to the patients health record.

Figure 4:
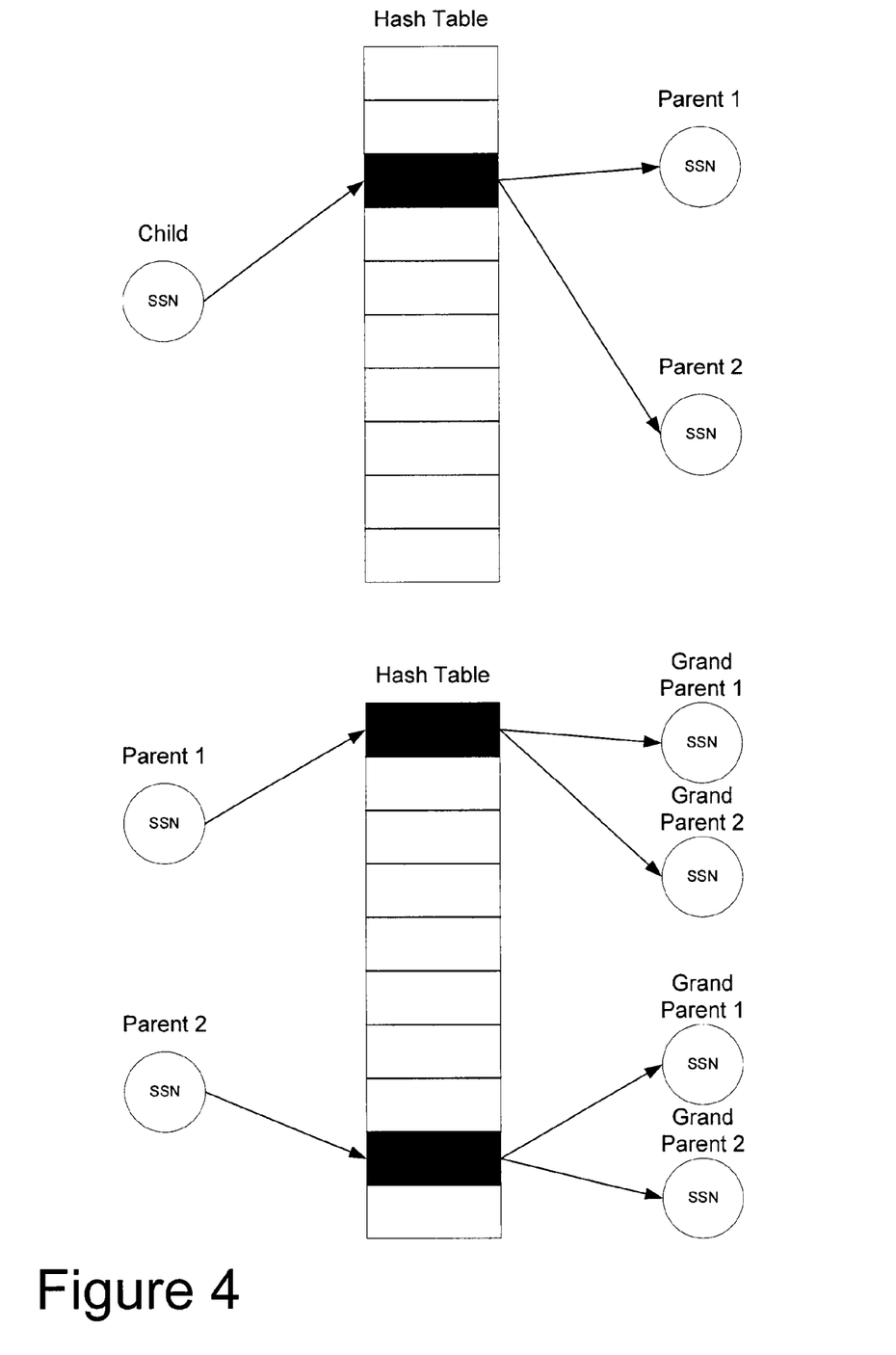
FIG. 4 is a diagram of retrieving parent health records obtained from hash keys stored within a child health record.

In another embodiment, a patients health record may contain the social security numbers of their mother, father, as well as other immediate family. These additional social security numbers can act as hash key to access the additional medical records of the mother, father, as well as other immediate family from the records database 411 as shown in FIG. 4. These additional records may also contain medical history, allergies, DNA information and other related medical information. This provides the health care provider with an extended medical history of the present individual in which more accurate and representative health care advice and treatment can be administered based on genetics and family history.

Figure 5:
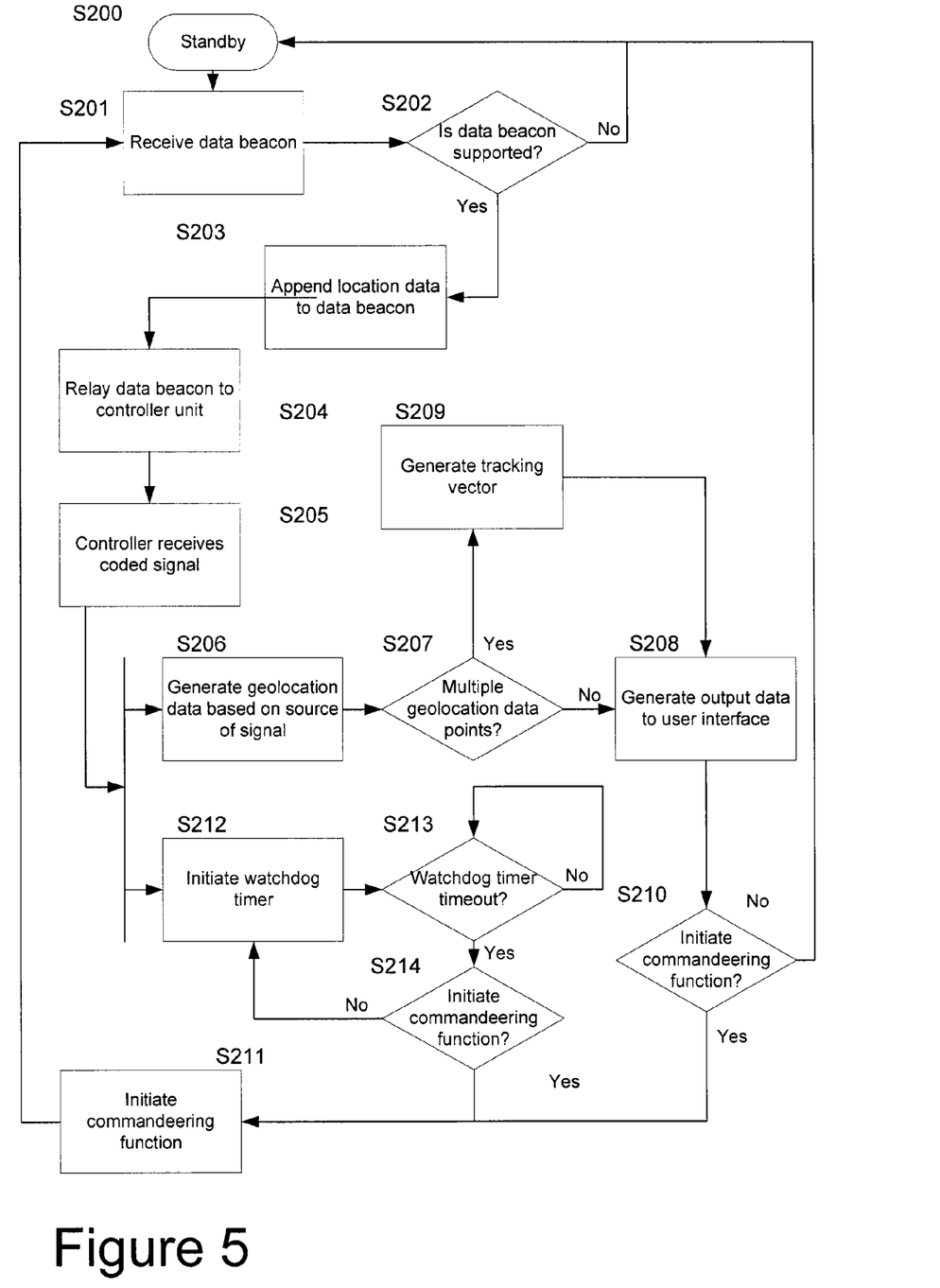
FIG. 5 is a flow chart of a process for generating geolocational data after receiving a beacon from a tracking chip in one embodiment of the present invention.

An exemplary process in which a transmitted message is broadcast from a tracking chip 10 to a pickup apparatus 20, relayed through a wireless network 30 to a controller unit 40, and processed within the controller unit 40 is shown in FIG. 5. Initially, a pickup apparatus 20 is standing by at S200 waiting to receive a beacon signal from a tracking chip 10. The data beacon can be received from a passive RFID chip at S201 by broadcasting a triggering signal or an applying an RFID signal. The data beacon can also be received from an active RFID chip at S201 which is autonomously broadcasting a beacon signal when the active RFID chip comes within range of the pickup apparatus 20. When a data beacon from the tracking chip 10 is received by the pickup apparatus 20, a determination is made at S202 whether the data beacon is of a supported format. The pickup apparatus 20 receiving the data beacon may not be the same pickup apparatus 20 that broadcast the triggering signal and may in fact be operating on a separate wireless network. At this point, it is unknown if the pickup apparatus receiving the data beacon supports the data format of the data beacon being broadcasted by the tracking chip 10. If a pickup apparatus 20 does not support the format of the data beacon, the data beacon is ignored. If it has been determined that the pickup apparatus 20 supports the data format of the received data beacon, the pickup apparatus 20 will append geolocation data to the data beacon at S203 and subsequently relay the data beacon to the controller unit 40 via an appropriate wireless network at S402. When the data beacon arrives at the controller unit 40 at S205, the message is demodulated and decoded.

The data beacon is then processed for geolocation data at S206. If this is the first piece of geolocation data that has been received from a specific tracking chip 10 as determined at S207, then the geolocation data is used to generate output data to the user interface at S208. If this is not the first piece of geolocation data from a specific tracking chip 10, then the geolocation data is used to update a tracking vector at S209 generated from previously received geolocation data from the same tracking chip 10. The updated tracking vector is used to generate output data to the user interface at S208. Based on the generated output of either the geolocational data or the tracking vector, the user has the option to initiate a commandeering function at S210 in order to attempt to actively prosecute the tracking chip 10 and generate additional geolocational data. If the user does not desire to actively prosecute the tracking chip at S210, the system will stand by for another data beacon to be sent at S200. If the user chooses to initiate a commandeering function at S210, the commandeering unit will generate a commandeering signal of an appropriate formatting at S211 based on the wireless network 30 in which the commandeering signal will be relayed to one or more pickup apparatus's.

At the same time that the initial geolocation data is processed at S206, a watchdog timer is initiated at S212. This timer generates a setting time for the corresponding piece of geolocation data. If the setting time exceeds a predetermined time specified by the user and triggers a watchdog timer timeout at S213, it is an indication that the most recent geolocation data is sufficiently out of date and may no longer be valid. In order to refresh the geolocation data, the signal geolocator unit has the option to automatically initiate the commandeering function at S214 in order to attempt to generate additional geolocation data. The user has the option to toggle on or off this automatic feature.

Figure 6:
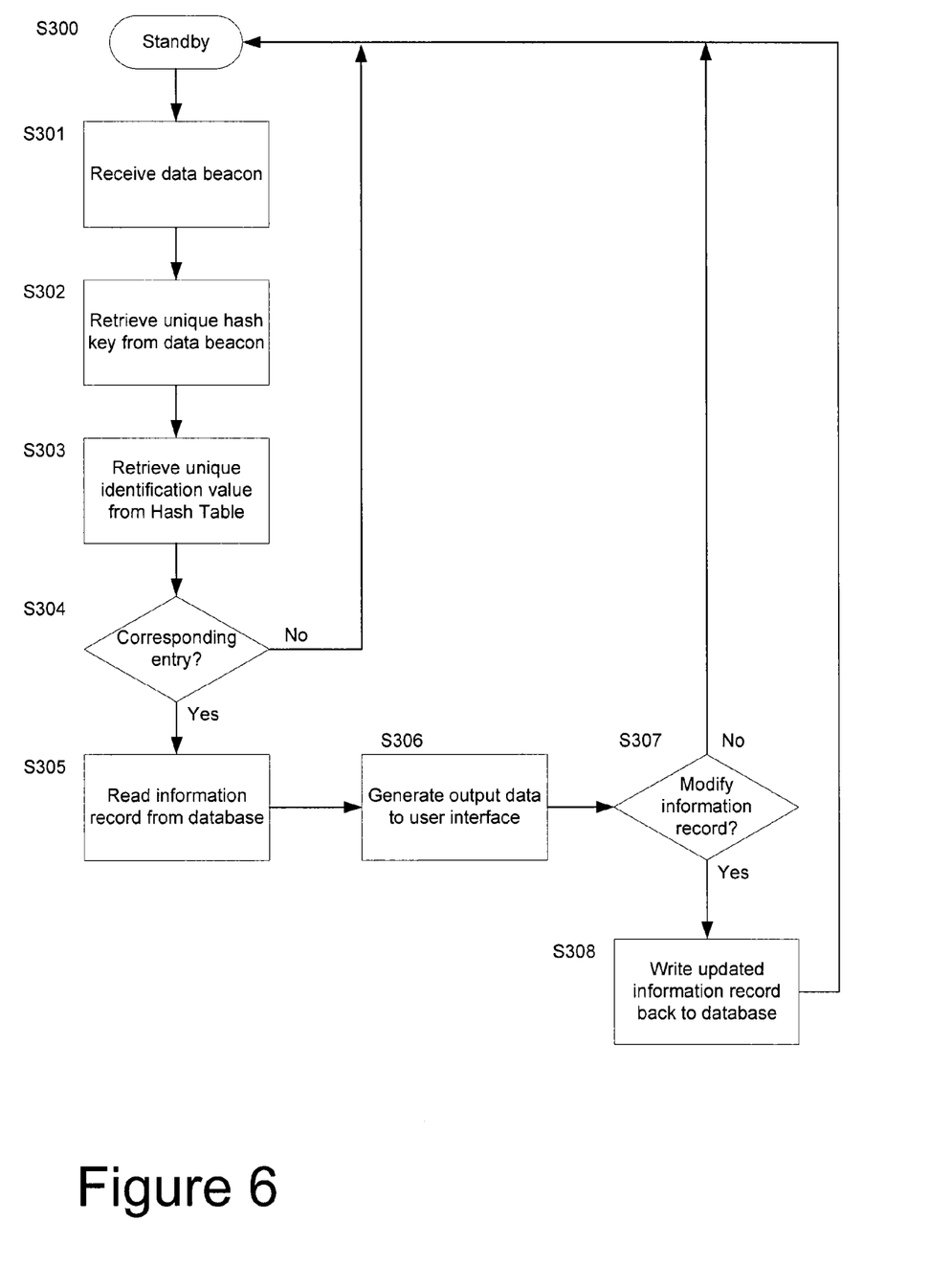
FIG. 6 is a flow chart of a process for retrieving a unique identification profile from a profile database in one embodiment of the present invention.

As an additional feature to the exemplary process of generating geolocation data and tracking vectors presented in FIG. 5, the controller unit 40 could also contain a process that retrieves a unique identification profile from a database that corresponds to a unique identification value included within the data beacon broadcasted by specific tracking chip 10 disposed with a human. This process is presented in FIG. 6. Initially, the controller unit 40 is standing by waiting for a data beacon to be received at the signal receiver 401 at S300. When a data beacon is received at S301, the data beacon is processed for to retrieve a unique hash key at S302. Once the unique hash key has been retrieved from the data beacon, the unique hash key is used as an input to a hash table in order to receive a unique identification value at S303. If no corresponding entry exists for the unique hash key at step S304, the system may assume that no entry exists and return to a standby state. If a corresponding entry does exist, the controller unit 40 will use the unique identification value obtained from the hash table to access the records database 411 and read the information record that corresponds to the unique identification value from the hash table at S305. The unique identification profile is presented to the user at S306 who has the option to view the record data as well as modify data within the record. If the user wishes to modify the data within the record at S307, the modified record will be written back to the record database at S308 and the system will return to the standby state.

In another embodiment, the hash key embedded within the transmission message is the social security number of the individual in which the tracking chip has been disposed. In other embodiments, however, the hash key can take the form of any random or non-random number sequence.

Figure 7:
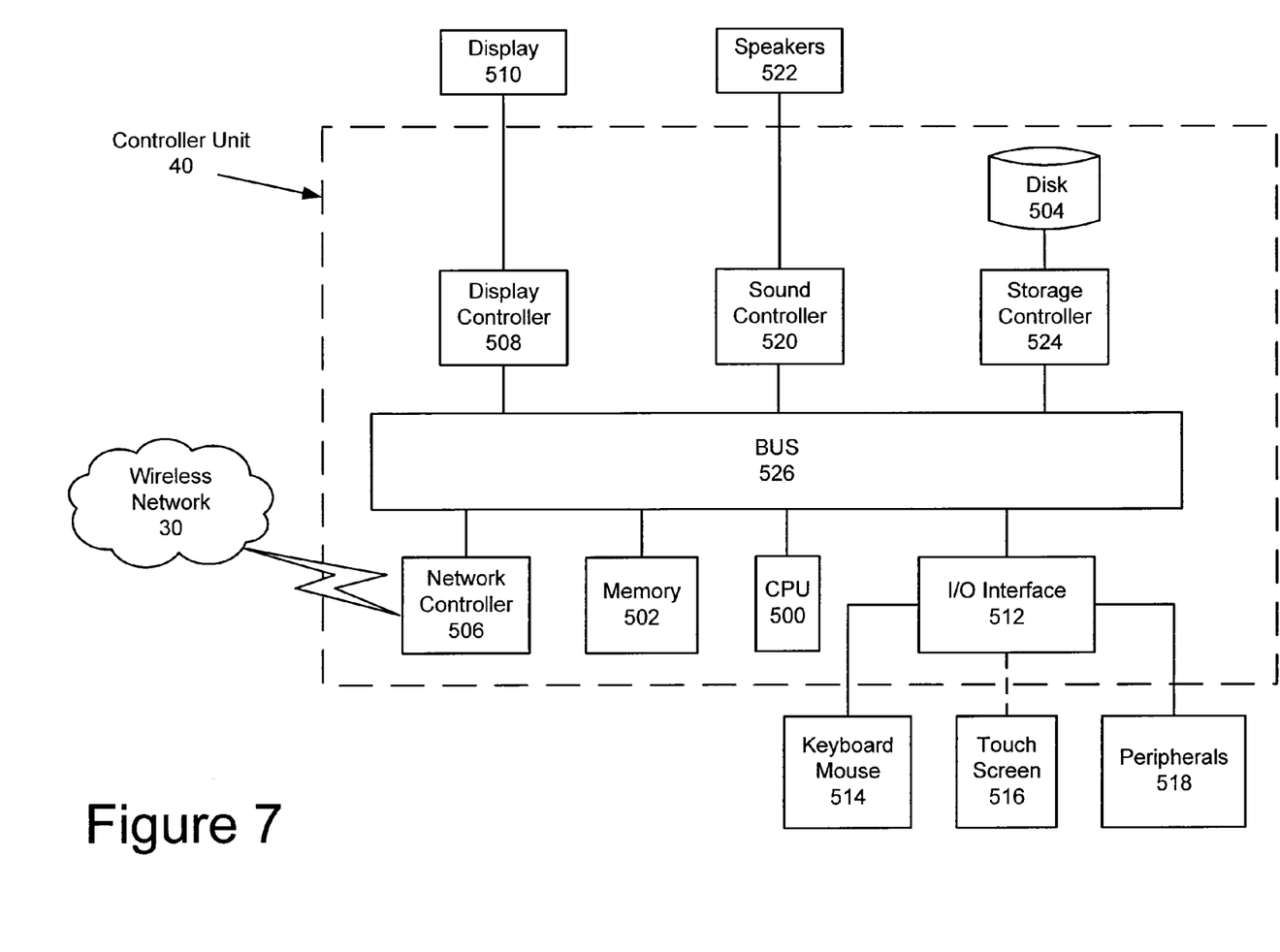
FIG. 7 is a hardware block diagram of an exemplary controller unit.

Next, a hardware description of the controller unit 40 according to exemplary embodiments is described with reference to FIG. 7. In FIG. 7, the controller unit 40 includes a CPU 500 which performs the processes described above. The process data and instructions may be stored in memory 502. These processes and instructions may also be stored on a storage medium disk 504 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer aided design station communicates, such as a server or computer.

Further, the claimed advancements may be provided as a utility application, background daemon, or component of an operating system, or combination thereof, executing in conjunction with CPU 500 and an operating system such as Microsoft Windows 7, UNIX, Solaris, LINUX, Apple MAC-OS and other systems known to those skilled in the art.

CPU 500 may be a Xenon or Core processor from Intel of America or an Opteron processor from AMD of America, or may be other processor types that would be recognized by one of ordinary skill in the art. Alternatively, the CPU 500 may be implemented on an FPGA, ASIC, PLD or using discrete logic circuits, as one of ordinary skill in the art would recognize. Further, CPU 500 may be implemented as multiple processors cooperatively working in parallel to perform the instructions of the inventive processes described above.

The controller unit 40 in FIG. 4 also includes a network controller 506, such as an Intel Ethernet PRO network interface card from Intel Corporation of America, for interfacing with wireless network 30. As can be appreciated, the wireless network 30 can be a public network, such as the Internet, or a private network such as an LAN or WAN network, or any combination thereof and can also include PSTN or ISDN sub-networks. The wireless network 30 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller unit 40 further includes a display controller 508, such as a NVIDIA GeForce GTX or Quadro graphics adaptor from NVIDIA Corporation of America for interfacing with display 510, such as a Hewlett Packard HPL2445w LCD monitor. A general purpose I/O interface 512 interfaces with a keyboard and/or mouse 514 as well as a touch screen panel 516 on or separate from display 510. General purpose I/O interface also connects to a variety of peripherals 518 including printers and scanners, such as an OfficeJet or DeskJet from Hewlett Packard.

A sound controller 520 is also provided in the controller unit 40, such as Sound Blaster X-Fi Titanium from Creative, to interface with speakers/microphone 522 thereby providing sounds and/or music. The speakers/microphone 522 can also be used to accept dictated words as commands for controlling the controller unit 40 or for providing location and/or property information with respect to the target property.

The general purpose storage controller 524 connects the storage medium disk 504 with communication bus 526, which may be an ISA, EISA, VESA, PCI, or similar, for interconnecting all of the components of the controller unit 40. A description of the general features and functionality of the display 510, keyboard and/or mouse 514, as well as the display controller 508, storage controller 524, network controller 506, sound controller 520, and general purpose I/O interface 512 is omitted herein for brevity as these features are known.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A mobile tracking and identification system comprising:
a tracking chip disposed in a human body of a first user and configured to passively transmit a data beacon via a wireless link once the tracking chip has been activated by a wireless triggering signal;
a pickup apparatus configured to generate the wireless triggering signal that activates the tracking chip and receive the data beacon generated from the tracking chip once activated, wherein the pickup apparatus is a private user equipment of a second user;
a wireless network configured to relay the data beacon from the pickup apparatus over a wireless transmission medium; and
a controller unit configured to receive the data beacon generated by the wireless network and generate geolocational data, store the geolocation data to produce a tracking vector, and initiate a commandeering function, wherein
the geolocational data is generated from receivable signals from GPS sources, local area network sources, and cellular sources each within a communication range of the tracking chip,
the tracking vector is determined using a predetermined weighted sum over present and past geolocational data from a GPS source, a local area network source, and a cellular source, and the controller unit initiates a handoff procedure by initiating a commandeering function of another pickup apparatus, when the tracking vector indicates that the pickup apparatus is leaving the communication range of the tracking chip, and the another pickup apparatus is in the communication range of the tracking chip, and the commandeering function initiates the transmission of the triggering signal of the pickup apparatus located within communication range of the tracking chip, and the pickup apparatus is commandeered from the second user for a limited time while the pickup apparatus is located within the communication range of the tracking chip.

2. The system of claim 1, wherein
the tracking chip is also configured to actively transmit the wireless data beacon without the activation of the tracking chip.

3. The system of claim 1, wherein
the pickup apparatus is one of a remote or mobile receiving unit specifically configured to recognize, detect, and communicate with the tracking chip.

4. The system of claim 1, wherein
the data beacon generated by the activated tracking chip contains a hash key that corresponds to a unique identification profile.

5. The system of claim 4, wherein
the hash key corresponds to a social security number of an individual.

6. The system of claim 4, further comprising:
a profile database that contains a plurality of unique identification profiles that contains personal information of individuals and configured to perform a profile lookup based on an output of a hash function using the hash key provided by the tracking chip.

7. The system of claim 6, wherein
the profile database includes a plurality of unique identification profiles, each of which contains individual health information of an original individual as well as additional hash keys corresponding to additional unique identification profiles that contain individual health information of one or more individuals relating to the original individual.

8. The system of claim 1, wherein
the tracking chip is constructed using nanotechnology.

9. The system of claim 1, wherein
the tracking vector is calculated from geolocation data from a plurality of pickup apparatus platforms using a weighted sum of the geolocation data across the plurality of pickup apparatus platforms, the calculation represented by the following equation:

$$\text{TrackingVector} = \Sigma(w_{GPS} \times \text{Data}_{GPS} + w_{WLAN} \times \text{Data}_{WLAN} + w_{CELL} \times \text{Data}_{CELL}).$$

10. A tracking method comprising:
transmitting a wireless data beacon via a wireless link, the wireless data beacon being generated from a passive tracking chip disposed within a human body of a first user once the tracking chip has been activated;
picking up the wireless data beacon from the tracking chip once it has been activated using a pickup apparatus, wherein the pickup apparatus is a private user equipment of a second user;
relaying the data beacon from the pickup apparatus to a controller over a wireless network via a wireless transmission medium;
receiving, at the controller, the data beacon from the wireless network;
generating geolocational data and a tracking vector of the tracking chip based on data contained within the data beacon received at the controller; and
initiating a commandeering function through one or more wireless networks to actively prosecute the a tracking chip, wherein
the geolocational data is generated from receivable signals from GPS sources, local area network sources, and cellular sources each within a communication range of the tracking chip,
the tracking vector is determined using a predetermined weighted sum over present and past geolocational data from a GPS source, a local area network source, and a cellular source, and the controller unit initiates a hand-off procedure by initiating a commandeering function of another pickup apparatus, when the tracking vector indicates that the pickup apparatus is leaving the communication range of the tracking chip, and the another pickup apparatus is in the communication range of the tracking chip, and
a commandeering function initiates the transmission of the triggering signal of the pickup apparatus located within the communication range of the tracking chip, and the pickup apparatus is commandeered from the second user for a limited time while the pickup apparatus located within the communication range of the tracking chip.

11. The method according to claim 10, wherein
the data beacon generated by the activated tracking chip contains a hash key that corresponds to a social security number of an individual.

12. The method according to claim 11, further comprising the step of:
accessing a profile database that contains a plurality of unique identification profiles that contains personal information of individuals and performing a profile lookup based on an output of a hash function using the hash key provided by the tracking chip.

13. The method according to claim 10, further comprising the steps of:
determining a communication protocol of the desired wireless network in which to transmit the commandeering signal;
transmitting a commandeering command to all eligible wireless devices within the desired wireless network of a designated region based on the communication protocol;
generating a list that contains all of the wireless devices on the wireless network that returned a response indicating that the device was able to be commandeered; and
transmitting a commandeering signal to all of the devices on the list, the commandeering signal commanding the wireless device to transmit a beacon that will activate the tracking chip disposed within a human body.

14. The method according to claim 10, wherein
the tracking vector is calculated from geolocation data from a plurality of pickup apparatus platforms using a weighted sum of the geolocation data across the plurality of pickup apparatus platforms and is represented by the following equation:

$$\text{TrackingVector} = \Sigma(w_{GPS} \times \text{Data}_{GPS} + w_{WLAN} \times \text{Data}_{WLAN} + w_{CELL} \times \text{Data}_{CELL}).$$

15. A non-transitory computer-readable storage device having program instructions stored therein that when executed by a processing circuit, implement a tracking method, the tracking method comprising:

transmitting a wireless data beacon via a wireless link and generated from a passive tracking chip disposed within a human body of a first user once the tracking chip has been activated;

picking up the wireless data beacon from the tracking chip once it has been activated using a pickup apparatus, wherein the pickup apparatus is a private user equipment of a second user;

relaying the data beacon from the pickup apparatus to a controller over a wireless network via a wireless transmission medium;

receiving, at the controller, the data beacon from the wireless network;

generating geolocational data and a tracking vector of the tracking chip based on data contained within the data beacon received at the controller; and initiating a commandeering function through one or more wireless networks to actively prosecute the a tracking chip, wherein the geolocational data is generated from receivable signals from GPS sources, local area network sources, and cellular sources each within a communication range of the tracking chip, the tracking vector is determined using a predetermined weighted sum over present and past geolocational data from a GPS source, a local area network source, and a cellular source, and the controller unit initiates a handoff procedure by initiating a commandeering function of another pickup apparatus, when the tracking vector indicates that the pickup apparatus is leaving the communication range of the tracking chip, and the another pickup apparatus is in the communication range of the tracking chip, and a commandeering function initiates the transmission of the triggering signal of the pickup apparatus located within the communication range of the tracking chip, and the pickup apparatus is commandeered from the second user for a limited time while the pickup apparatus located within the communication range of the tracking chip.

* * * * *